United States Patent [19]

Okai

[11] Patent Number: 4,613,458
[45] Date of Patent: Sep. 23, 1986

[54] REGULATORY SUBSTANCE OF DNA SYNTHESIS

[75] Inventor: Yasuji Okai, Machida, Japan

[73] Assignee: Kyowa Hakko Kogyo Co., Ltd., Tokyo, Japan

[21] Appl. No.: 662,287

[22] PCT Filed: Feb. 1, 1984

[86] PCT No.: PCT/JP84/00029

§ 371 Date: Sep. 26, 1984

§ 102(e) Date: Sep. 26, 1984

[87] PCT Pub. No.: WO84/03104

PCT Pub. Date: Aug. 16, 1984

[30] Foreign Application Priority Data

Feb. 2, 1983 [JP] Japan .................................. 58-15790

[51] Int. Cl.$^4$ ............................................. C07K 15/06
[52] U.S. Cl. .................................... 530/351; 435/68; 435/240; 424/95
[58] Field of Search ............. 260/112 R; 435/68, 240; 424/95

[56] References Cited

PUBLICATIONS

Regulatory Serum . . . Lipo Protein, *J. Immunology* 116(5) 1976, p. 1452, Curtis et al.
The Effect of Immunogulation . . . in vitro, *J. Immunol* 109(1) 1972, p. 154, Cooperband et al.
C.A. No. 21197p vol. 101, 1984 DNA Synthesis Inhibitor Block Protein Synthesis . . . , Lymphocyte, Albert et al.
C.A. No. 154526w, vol. 100, 1984, Purifed Plasma . . . 3T3 Cells, Vale et al.
C.A. No. 20457g, vol. 92, 1979, Normal Immunosuppressive Protein . . . Cell Line, Ovodia et al.

*Primary Examiner*—John Kight
*Assistant Examiner*—Garnette D. Draper
*Attorney, Agent, or Firm*—Fitzpatrick, Cella, Harper & Scinto

[57] ABSTRACT

Regulatory substance of T cell DNA synthesis comprising low molecular peptide having the following physicochemical properties:

(a) Elementary analysis: Having the elements C, H, O, N and S
(b) Molecular weight: About 1,000 daltons
(c) pH stability: Stable at pH 3.5–10.0
(d) Ultraviolet spectrum: Maximum absorption at 210–220 nm
(e) Color reaction: Ninhydrin positive The present substance is produced from fibroblasts or lymphocytes of animals, fibroblasts of insects, serum of animals and body fluids of insects.

The present substance regulates the activity of immunocompetent cells and is useful for the treatment of autoimmune diseases.

9 Claims, 19 Drawing Figures.

REGULATORY SUBSTANCE OF DNA SYNTHESIS

TECHNICAL FIELD

The present invention relates to a novel regulatory substance of T cell DNA synthesis. More specifically, the present invention relates to regulatory substances of T cell DNA synthesis obtained by culturing fibroblasts or lymphocytes of animals or insects in a medium free of serum or containing bovine fetal serum or by recovering from the serum of animals or body fluids of insects.

BACKGROUND ART

Heretofore, steroids, immuran, and the like have been used for the treatment of various autoimmune diseases caused by unusual acceleration of immune activity in immunocompetent cells such as T cells. Although these drugs have considerable therapeutic effects upon certain diseases, they have side-effects such as adrenal insufficiency and leukopenia against normal cells. Therefore, more excellent drugs are still in demand.

The present inventors have found that fibroblasts and lymphocytes of animals produce a substance which regulates the DNA synthesis of immunocompetent cells such as T cells and that the substance regulates the activity of immunocompetent cells and is useful for the treatment of autoimmune diseases. Thus the present invention has been completed Regulatory substances against immunocompetent cells have been reported in J. Immunol 109, 154–163 (1972), J. Immunol 116, 1452–1458 (1976) and Inflammation 1, 5–21 (1975). Since these known substances are high molecular substances, they have possibility of bringing about side-effects such as immuno-refusal effect of patients. The substance of the present invention is low molecular peptide derived from mammals and therfore, is expected to produce less side-effect and to be applicable to immuno-diseases.

DISCLOSURE OF THE INVENTION

The novel regulatory substance of T cell DNA synthesis of the present invention (referred to as "the present substance" hereinafter) is obtained by culturing fibroblasts or lymphocytes of animals or insects in a medium and recovering the present substance accumulated in the culture medium.

As the animal, mammals such as mouse, rat, human and the like are preferably used. As the cells, mouse C3H/He spleen cells, mouse 3T3 fibroblasts [J. Cell Biol., 17, 299 (1963)], rat spleen cells SD (Splague Dawley) and human fetal fibroblasts are preferably used. These cells can be obtained from Seiwa Jikken Dobutsu Co., Ltd., Ohita.

As the cells of insects, fibroblasts established from *Antheraea eukarypti* [Grace, Nature, 195, 788 (1962)] are preferably used.

As the medium, any medium employable for the culture of animal cells may be used. Preferably, RPMI 1640 medium, MEM medium, and the like are used. The compositions of RPMI 1640 medium and MEM medium are described in "Soshiki Baiyo (Tissue Culture)" edited by Junnosuke Nakarai, et al., published by Asakura Shoten, pages 9–11, 1976. 1–10% bovine fetal serum may be added to the medium. Addition of phorbol esters to the medium increases the productivity of the present substance.

As the phorbol esters, phorbol myristate, phorbol-13acetate and 12-O-tetradecanoyl-phorbol-13-acetate (TPA) are preferably used.

The phorbol esters are generally used in a concentration of 1–1,000 ng, preferably 10–100 ng per 1 ml of culture medium.

Culturing is carried out under aeration in a liquid medium according to conventional culture conditions for animal cells. 5–10% $CO_2$ and 90–95% air are aerated. Culturing temperature is 25°–40° C., preferably 30°–37° C., pH is 7.5–8.5, preferably 7.8–8.0 and culturing time is preferably 5–24 hours. Recovery of the regulatory substance of T cell DNA synthesis from culture medium is carried out according to a conventional method used for recovering proteins from culture medium of animal cells.

After culturing, cells are removed by centrifugation to recover the culture supernatant. Twice as much saturated ammonium sulfate (pH 7.5) as the supernatant by volume is added thereto and subjected to salting-out. The salting-out material is centrifuged and the resulting precipitate is dissolved in a physiological saline solution. The solution is subjected to Sephadex G 100 column chromatography and elution with physiological saline solution. A regulating activity against T cell DNA synthesis is recognized in a fraction containing a low molecular substance. The active fraction is diluted with twice as much distilled water as the fraction by volume and subjected to CM Sephadex column chromatography. The column is washed with 50 mM saline solution and elution is carried out under gradient of the concentration of saline solution.

The present substance is eluted out with about 400 mM saline solution. The active fraction is concentrated with a rotary evaporator. The concentrate is subjected to Sephadex G 50 column chromatography and elution is carried out with physiological saline solution. Activity is recognized at a molecular weight of about 1,000 daltons and the active fraction is concentrated with a rotary evaporator. The concentrate is subjected to silica gel thin layer chromatography which is developed with a methanol-water solvent to recognize two ninhydrin positive spots. The regulating activity against T cell DNA synthesis is contained in the spot with lower mobility. The silica gel of the spot is recovered and the present substance is extracted with water.

The present substance can also be obtained by recovering from the serum of mammals or body fluids of insects.

As the serum of mammals, the serums of humans, bovines, rats, mice and the like are employed. As the body fluids of insects, the body fluid of insects belonging to Lepidoptera, Diptera, Hymenoptera and the like, such as Bombyx, Antheraea, Sarcophaga and Apis are employed.

The recovery of the present substance from the serum of mammals or body fluids of insects is carried out by the same method as in the recovery of the present substance from the culture supernatant mentioned above.

DNA synthesis activity of T cell is measured by the following method during the recovery.

$2.5 \times 10^5$ thymus cells of C3H/He mouse are suspended in 0.1 ml of RPMI 1640-10% fetal calf serum. The suspension is mixed with 0.1 ml of the supernatant of fibroblast culture or each fraction of the column chromatography. 2.5 µg/ml concanavalin A is added and the mixture is cultured in vitro for 2 days. The culture medium is pulse-labelled with 1 μCi of [³H]-thymidine for the last 20 hours of culturing and the amount of [³H]-thymidine incorporated in the thymus cell is measured.

The thus obtained present substance is a low molecular peptide having the following physicochemical properties.

(1) Elementary analysis: Having the elements C, H, O, N and S
(2) Molecular weight: About 1,000 daltons
(3) Thermostability (pH 6.6–6.7): Stable for several months at −20° C., for 30 minutes to 1 hour at 56° C. and for 30 minutes at 100° C.
(4) Distinction on acidic, basic, or neutral properties: Weakly basic
(5) pH stability (25° C.): Stable at pH 3.5–10.0
(6) Ultraviolet spectrum: Maximum absorption at 210–220 nm (refer to FIG. 5)
(7) Color reaction: Ninhydrin positive
(8) Solubility in solvents: Readily soluble in water, ethanol and methanol
(9) Color of substance: Colorless in the solvent mentioned above
(10) The regulatory activity against T cell DNA synthesis disappears by the treatment with 25 μg/ml trypsin at 37° C. for 1 hour.
(11) The regulatory activity against T cell DNA synthesis is not affected by the treatments with 25 μg/ml ribonuclease A and 25 μg/ml deoxyribonuclease I, respectively, at 37° C. for 1 hour.

Biological activities of the present substance are determined in the following manner.

Determination of the activity of DNA synthesis in the lymphocytes and other cells of mammals $5 \times 10^5$ spleen cells or thymus cells of C3H/He mouse are suspended in RPMI 1640 medium (product of Nissui Seiyaku Co.) containing 10% fetal calf serum (product of GIBCO). In the presence of concanavalin A (product of Sigma Co., final concentration 5 μg/ml), the mixture is cultured under aeration with 5% $CO_2$ and 95% air for 3 days. Before the completion of culturing, cells are labelled with 1 μCi of [³H] thymidine (product of Radiochemical Center, England) for one day. The cells are trapped on the GF/C or GF/F membrane filter (product of Whatman Co.) using a cell harvester. The membrane is washed with water and ethanol and dried. The activity of [³H] thymidine incorporated in the cells is determined with Beckman Scintillation Counter.

Determination of the activity of DNA synthesis in other cells of mammals is carried out by the following method. $1 \times 10^4$ cells are suspended in 0.1 ml of RPMI 1640 medium containing 10% fetal calf serum and after addition of 0.1 ml of a fraction of sample, the mixture is cultured in the absence of concanavalin A for 24 hours. The cells are labelled with 1 μCi of [³H] thymidine for 8 hours before the completion of culturing. The other conditions are the same as those employed in the case of lymphocytes.

Determination of the activity of nucleotide uptake by lymphocytes

In order to examine the action of the regulatory substance of DNA synthesis upon the function of cell membranes, the activity of nucleotide uptake, herein uridine triphosphate (referred to as UTP hereinafter) uptake is determined. Spleen cells of mouse are cultured under the same conditions as in the determination of the activity of DNA synthesis described above and cells are labelled with 1 μCi of [³H] UTP (product of Radiochemical Center) at the start of culturing. The determination of activity is carried out by the same method as mentioned above.

Determination of the activity of DNA synthesis in bacteria

10 μl of a suspension (0.5A 660 nm) of bacteria such as *Escherichia coli*, *Pseudomonas maltophilia* and *Bacillus subtilis* is diluted with 90 μl of RPMI 1640 medium containing 5% fetal calf serum and 0.1 ml of each fraction is added. 1 μCi of [³H] thymidine is added and the bacteria are cultured at 37° C. overnight (16 hours). The bacteria are trapped on GF/C membrane filter and thymidine uptake is determined by the same method as mentioned above.

The mechanism of action of the present substance on T cells is as follows.

Survival of T cells after the addition of the present substance, which is determined by dye exclusion method using Trypan Blue, is equivalent to that of T cells free of the substance. That is, the present substance does not principally kill T cells but regulates only the DNA synthesis in T cells (refer to Experiment 1 and Table 1).

The activity of the present substance regulating the DNA synthesis is largest in mammal lymphocytes and significantly large in mammal fibroblast cells. The activity is not recognized in carcinoma cells. The activity against bacteria is large in *Escherichia coli* which is a Gram negative bacterium and low in *Bacillus subtilis* which is a Gram positive bacterium. The assumed mechanism of the regulation against DNA synthesis in lymphocytes is that the present substance regulates the function of the cell membrane, for example, transmission activity of nucleotides, at comparatively early stage after lectin stimulation and the DNA synthesis thereafter is specifically regulated. The present substances regulate strongly DNA synthesis but do not affect survival ratio of cells.

The present substance does not regulate T cell RNA synthesis (refer to Experiment 2 and FIG. 6) but regulates significantly the activity of nucleotide uptake of T cells at the early stage (0–5 hours) (refer to FIG. 6a).

The regulation of the function of cells at the early stage (the regulation of nucleotide uptake at the early stage) by the present substance is considered to be due to the regulation of T cell DNA synthesis (refer to Experiment 3 and Table 2).

Experiment 1

Effect of the present substance on the survival ratio of T cells:

$5 \times 10^6$ thymus cells of C3H/He mouse were suspended in 1 ml of RPMI 1640 medium-5% fetal calf serum, and 0.1 ml of the present substance or 0.1 ml of physiological saline solution as a control was added to the suspension. After one and two days, the survival ratio of the cells was determined by dye exclusion method wherein 0.1 ml of cell suspension was diluted 20 times with 1.9 ml of 0.1% Trypan Blue solution after one and two days and the cells stained with Trypan Blue were counted under a microscope.

The result is shown in Table 1.

TABLE 1

| Test No. | Incubation time (day) | Control Cells (× 10⁵) | Control Survival (%) | Treated with the present substance Cells (× 10⁵) | Treated with the present substance Survival (%) |
|---|---|---|---|---|---|
| 1 | 1 | 3.6 | 72 | 3.8 | 76 |
|   | 2 | 2.1 | 42 | 2.0 | 40 |
| 2 | 1 | 3.4 | 68 | 3.3 | 66 |
|   | 2 | 1.9 | 38 | 1.6 | 32 |

EXPERIMENT 2

Mechanism of action of the present substance on T cells:

$5 \times 10^5$ thymus cells of C3H/He mouse were suspended in RPMI 1640 medium-5% fetal calf serum, and 5 µg/ml concanavalin A was added to make the final volume 0.1 ml, followed by the addition of 0.1 ml of active fraction. Then 1 µCi of [$^3$H] UTP was added to the culture to label RNA in the cells. Reaction was stoped with cooled 10% trichloroacetic acid (TCA) at intervals and the RNA in the fraction insoluble in TCA was trapped on a GF/F membrane filter (product of Whatman Co.). The membrance was washed repeatedly with 5% TCA and once with ethanol. The membrane was then dried and put in toluene-POP solution. Radioactivity of the RNA fraction was measured with a β-scintillation counter to determine the ability of RNA synthesis.

The result is shown in FIG. 6, wherein (a) shows the activity of uptaking [$^3$H] UTP into T cells and (b) the activity of RNA synthesis. In FIG. 6, open circle shows the result in the absence of the present substance and closed circle the result in the presence of the present substance.

EXPERIMENT 3

Effective addition time of the present substance for the regulation of DNA synthesis $2.5 \times 10^5$ thymus cells of C3H/He mouse were suspended in RPMI 1640 medium-5% fetal calf serum containing 5 µg/ml concanavalin A to make the final volume 0.1 ml. The suspension was cultured at 37° C. under aeration with 5% CO₂ and 95% air for 3 days. During the culturing, 0.1 ml of the present substance was added at the time shown in Table 2. The cells were labelled with 1 µCi of [$^3$] thymidine 12 hours before the completion of the culturing and the activity of [$^3$] thymidine uptaken into the cells was measured.

The results are shown in Table 2.

TABLE 2

| Addition time | [$^3$H] thymidine uptake (CPM) | Relative activity % |
|---|---|---|
| — | 3742 ± 234 | 100.0 |
| 0 | 524 ± 102 | 14.0 |
| 2.5 | 507 ± 191 | 13.5 |
| 5 | 509 ± 65 | 13.6 |
| 15 | 903 ± 178 | 24.1 |
| 30 | 3218 ± 203 | 86.0 |

Experiment 4

Effect of the present substance on various mammal cells:

The effects of the present substances on mammal cells were examined by the method described above.

The results are shown in Tables 3 and 4.

TABLE 3

Effect of the present substance (FCS I) derived from fetal calf serum on various mammal cells

| Target cell | [$^3$H] thymidine uptake (CPM) Control | [$^3$H] thymidine uptake (CPM) FCS I |
|---|---|---|
| GM258 (human fibroblast) | 2341 | 482 |
| IMR90 (the same as above) | 5029 | 2312 |
| SV40-transformed cell (the same as above) | 9193 | 9005 |
| PC10 (human lung carcinoma) | 9124 | 8923 |
| L929 (mouse fibrosarcoma) | 4056 | 4219 |
| MeLa3 (human melanoma) | 4392 | 4155 |
| Mouse spleen cell | 22180 | 698 |
| Mouse thymus cell | 3689 | 392 |

TABLE 4

Effect of the present substance (Ae I) derived from Antheraea eukarypti on various mammal cells

| Target cell | [$^3$H] thymidine uptake (CPM) Control | [$^3$H] thymidine uptake (CPM) Ae I |
|---|---|---|
| GM258 | 1467 | 260 |
| IMR90 | 5512 | 2659 |
| SV40-transformed cell | 9689 | 9321 |
| PC10 | 9065 | 9215 |
| L929 | 4367 | 4528 |
| MeLa3 | 5978 | 4862 |
| Mouse spleen cell | 16850 | 1721 |
| Mouse thymus cell | 3415 | 289 |

Experiment 5

Effect of the present substance on bacterial DNA synthesis:

The effects of the present substances on bacterial DNA synthesis were examined by the method described above.

The results are shown in Table 5.

TABLE 5

Effect of the present substances on bacterial DNA synthesis

| Bacteria | [$^3$H] thymidine uptake (CPM) $\left[\frac{\text{the present substance}}{\text{Control}} \%\right]$ FCS I | [$^3$H] thymidine uptake (CPM) $\left[\frac{\text{the present substance}}{\text{Control}} \%\right]$ Ae I |
|---|---|---|
| Escherichia coli | 12.4 | 5.1 |
| Bacillus subtilis | 88.3 | 88.9 |
| Pseudomonas maltophilia | 71.0 | 96.5 |

The present substance is a low molecular peptide which regulates strongly T cell DNA synthesis and therefore, is useful as the therapeutic agent for autoimmune diseases and as the regulatory agent against abnormal activation of lymphocytes such as inflammation. Since the present substance regulates only DNA synthesis and does not kill T cells, it can be applied to regulate specifically DNA synthesis. Further, as the productivity of the present substance is raised by making the cells producing the present substance precancerous with phorbol esters, the present substance can be applied as a marker for the diagnosis of cancer. Furthermore, the present substance is employed as anti-bacterial agent specifically against Gram negative bacteria.

BEST MODE FOR CARRYING OUT THE INVENTION

EXAMPLE 1

Production of the present substance by fibroblasts of 3T3 mouse:

$10^8$ fibroblasts of 3T3 mouse were inoculated into $10^8$ of RPMI 1640 medium (product of GIBCO) containing 100 μg/ml streptomycin, 100 units/ml penicillin and 5% FCS (fetal calf serum, product of GIBCO), and culturing was carried out at 37° C. under aeration with 5% $CO_2$ and 95% air for 3 days. The fibroblasts of 3T3 mouse attained a saturated cell concentration, so-called confluent condition, by the culturing.

Figure 1:
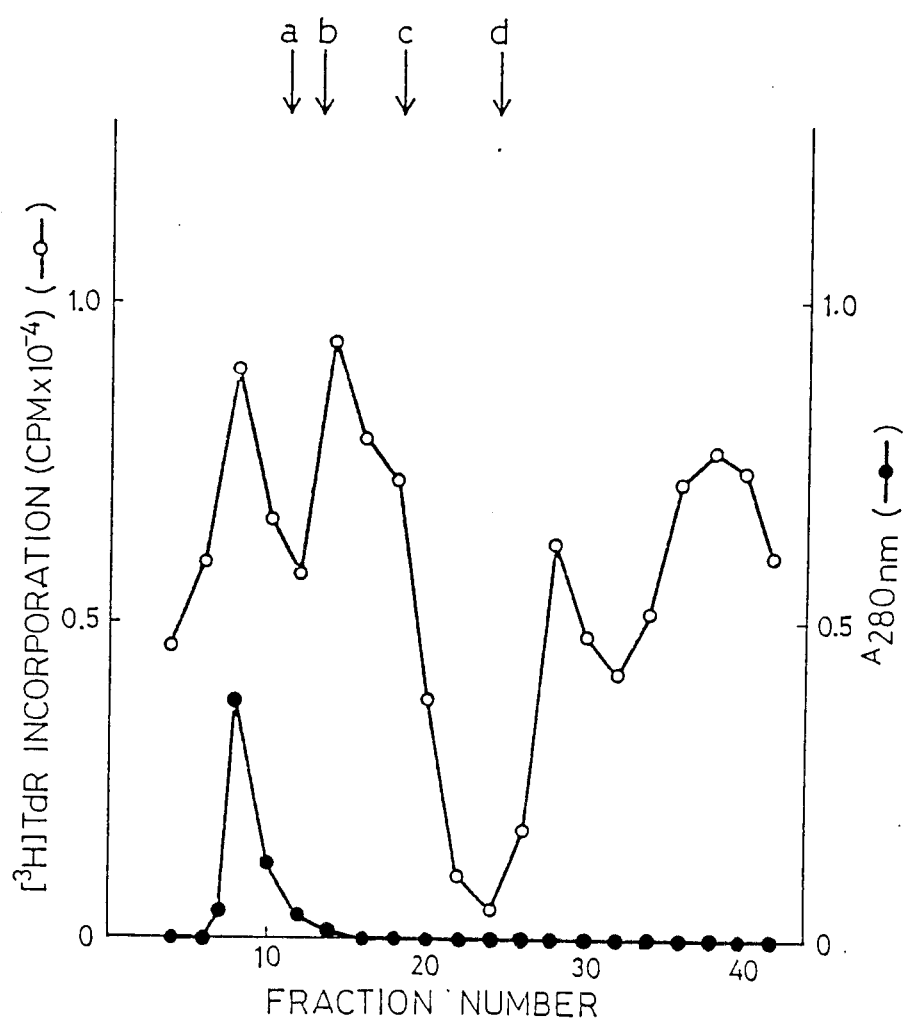
FIG. 1 shows Sephadex G 100 column chromatogram for the purification of the present substance in Example 1. Arrows a, b, c and d refer to the markers of albumin (67 kilodaltons, referred to as Kd hereinafter), horseradish peroxidase (40 Kd), cytochrome C (13 Kd) and bacitracin (1.5 Kd), respectively. The same meanings are employed hereinafter.

Supernatant fluid was removed from the culture medium and 10 ml of fresh RPMI 1640 medium free of serum was added. Culturing was carried out at 37° C. under aeration with 5% $CO_2$ and 95% air for 10 hours. Supernatant fluid of the culture medium was recovered and twice as much saturated ammonium sulfate (pH 7.5) as the supernatant was added. The mixture was subjected to salting-out and the salting-out material was centrifuged to obtain a precipitate. The precipitate was dissolved in a small amount of physiological saline solution and subjected to Sephadex G 100 column (2 ml) chromatography. Elution was carried out with physiological saline solution and the eluate was recovered in 2.5 ml fractions. As illustrated in FIG. 1, a strong inhibitory activity against T cell DNA synthesis was recognized in a fraction containing a low molecular substance.

Figure 2:
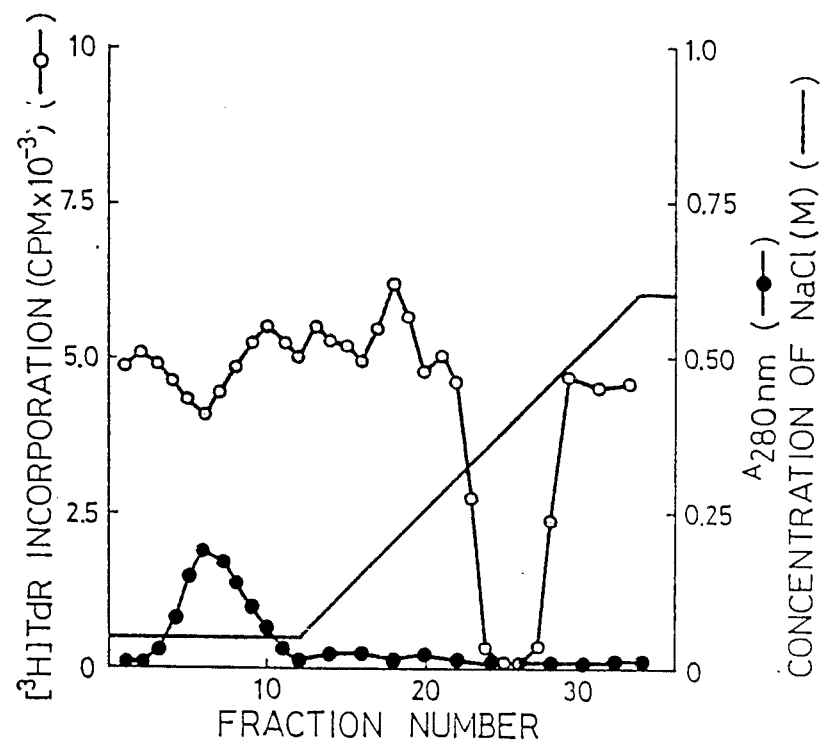
FIG. 2 shows CM Sephadex column chromatogram for the purification of the present substance in Example 1.
Figure 3:
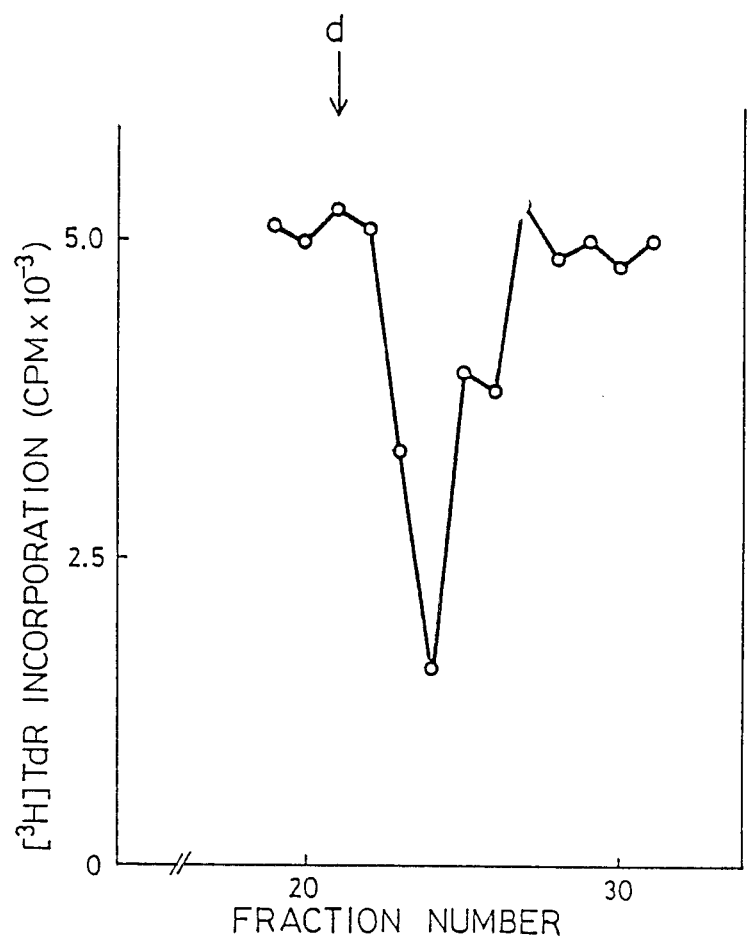
FIG. 3 shows Sephadex G 50 column chromatogram for the purification of the present substance in Example 1.
Figure 4:
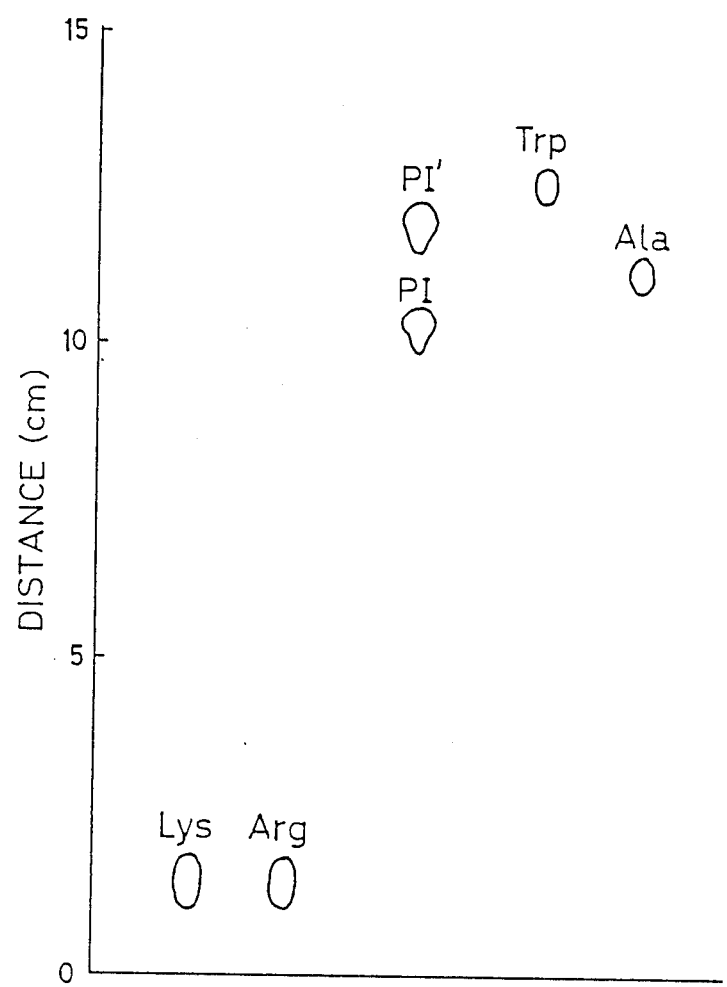
FIG. 4 shows silica gel thin layer chromatogram of the active fraction in Example 1 and amino acid markers.
Figure 5:
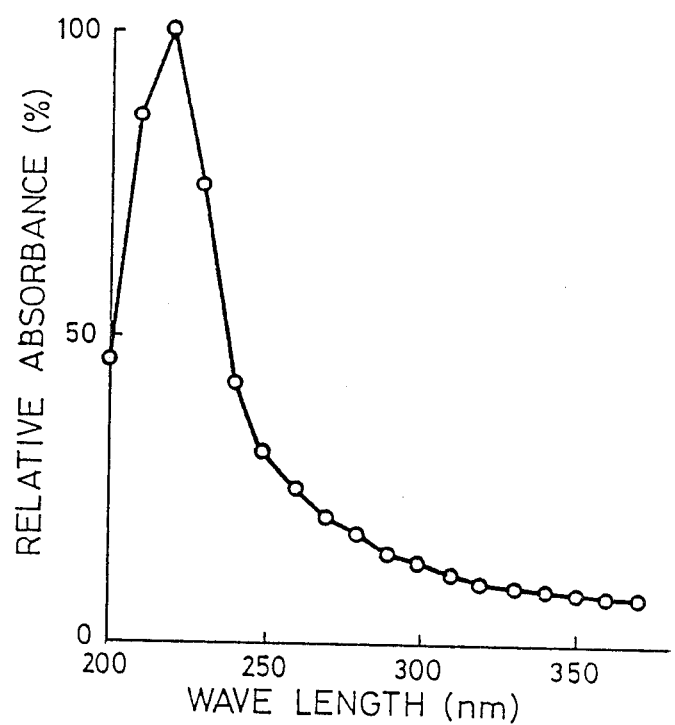
FIG. 5 shows ultraviolet absorption spectrum of the present substance.
Figure 6:
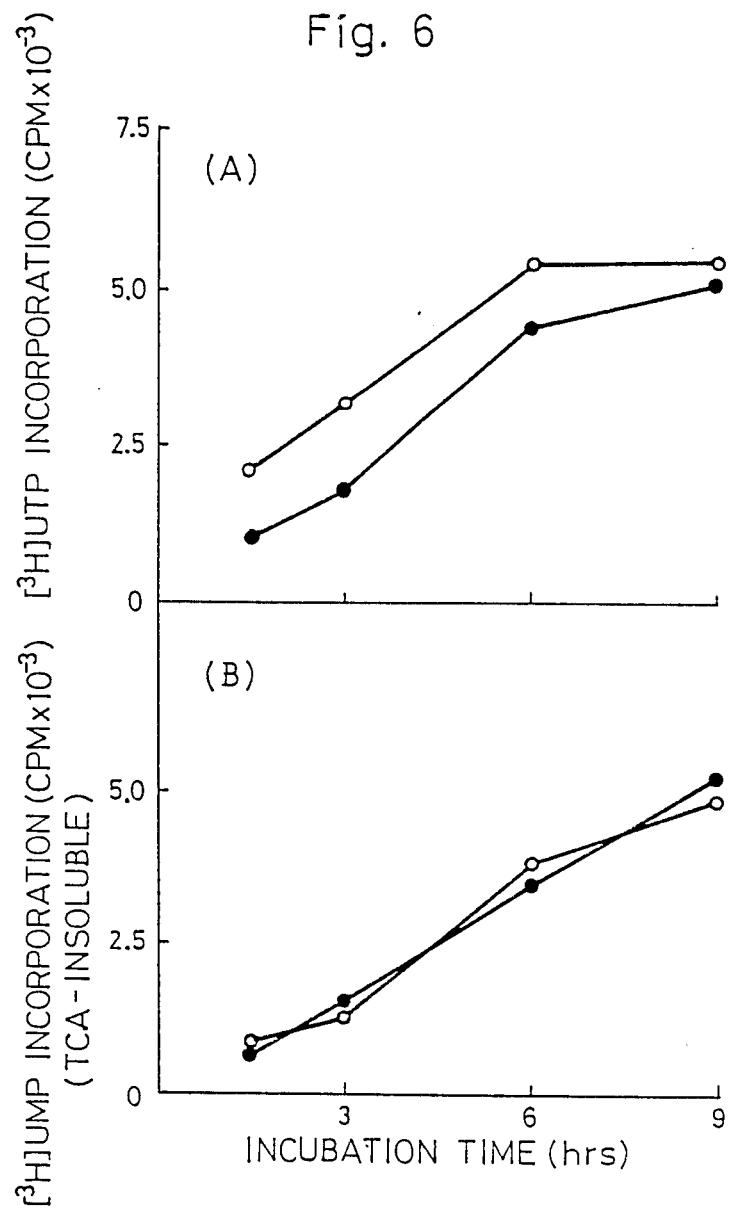
FIG. 6 shows the mechanism of action of the present substance on T cells. Open circle refers to non-treatment and closed circle refers to treatment with the present substance.

The active fraction was diluted with twice as much distilled water as the fraction and subjected to CM Sephadex column chromatography. After washing with 50 mM saline solution, elution was carried out under gradient of the concentration of saline solution (50-600 mM) and the eluate was recovered in 1.5 ml fractions. As illustrated in FIG. 2, the active substance was eluted mainly with about 0.4 M saline solution. 9 ml of the active fraction was concentrated at 50° C. with a rotary evaporator to 0.5 ml. The concentrate was subjected to Sephadex G 50 column chromatography and elution was carried out with physiological saline solution. The eluate was recovered in 1.25 ml fractions. As illustrated in FIG. 3, the activity was recognized in a fraction containing a substance with a molecular weight of about 1,000 daltons. The active fraction was developed by silica gel thin layer chromatography. As illustrated in FIG. 4, there were two spots positive to ninhydrin reaction, PI and PI', and a strong regulatory activity against T cell DNA synthesis was recognized in PI.

Activities of PI and PI' are shown in Table 6. The silica gel of PI was recovered and the present substance was extracted with water, followed by lyophilization to obtain 5 μg of the present substance. PI corresponds to the present substance.

TABLE 6

|  | [$^3$H] thymidine uptake (CPM) |
| --- | --- |
| Control | 5627 ± 231 |
| PI' | 5456 ± 629 |
| PI | 821 ± 105 |

EXAMPLE 2

Figure 7:
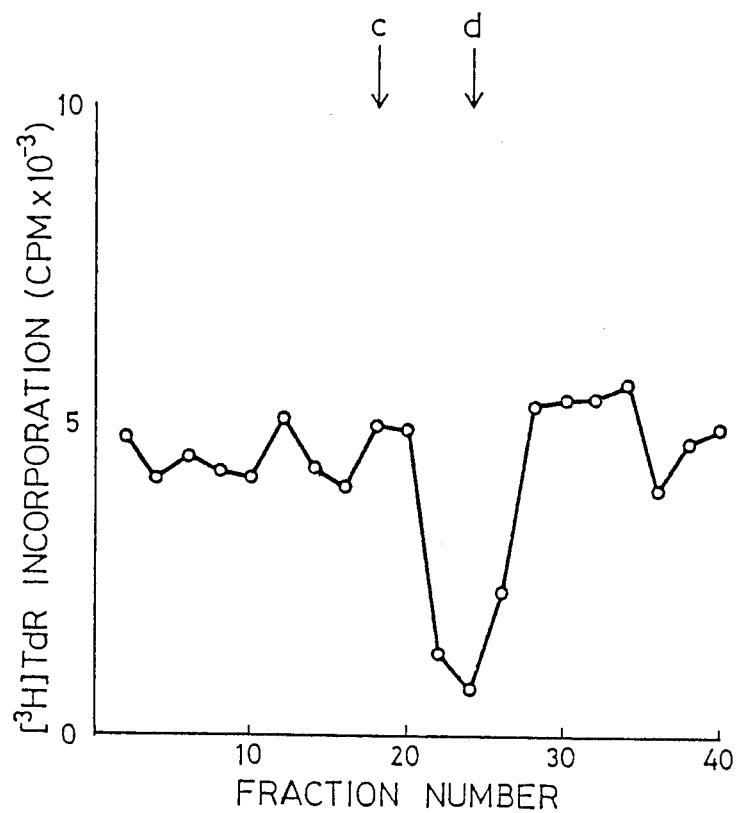
FIG. 7 shows Sephadex G 100 column chromatogram for the purification of the present substance in Example 2.

Production of the present substance by mouse spleen cells:

$10^8$ spleen cells of C3H/He mouse were suspended in 10 ml of RPMI 1640 medium and culturing was carried out at 37° C. under aeration with 5% $CO_2$ and 95% air for 10 hours. The supernatant fluid was subjected to Sephadex G 100 column chromatography and elution in the same manner as in Example 1. As illustrated in FIG. 7, a strong inhibitory activity against T cell DNA synthesis was recognized in a fraction containing a low molecular substance.

The active fraction was subjected to CM Sephadex column chromatography in the same manner as in Example 1 and elution was carried out with 0.4 M NaCl.

Figure 8:
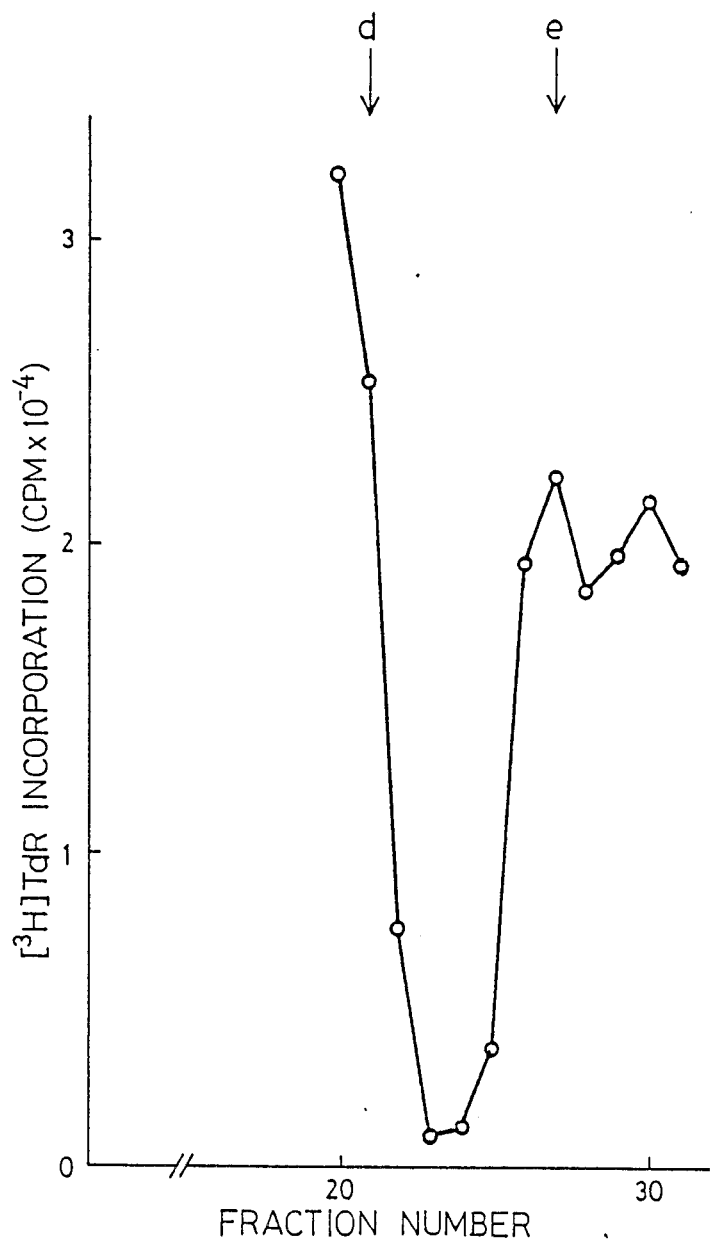
FIG. 8 shows Sephadex G 50 column chromatogram for the purification of the present substance in Example 2. Arrow e refers to the marker of mitomycin C (340 daltons). The same meaning is employed hereinafter.

An active fraction was further subjected to Sephadex G 50 column chromatography. As illustrated in FIG. 8, an activity was recognized at the same position as in Example 1. The active fraction was developed by silica gel thin layer chromatography in the same manner as in Example 1, followed by purification to obtain about 20 μg of the present substance.

EXAMPLE 3

Production of the present substance by human fetal fibroblasts:

Two months old human fetal embryo was treated with trypsin and inoculated into MEM medium (product of Nissui Seiyaku Co.) containing 10% FCS, 10 mM N-N-bis (2-hydroxyethyl)-2-aminoethane-sulfonate (BES), 5 mM N-tris (hydroxymethyl)-methyl-2-aminopropane-sulfonate (TES) and 5 mM N-hydroxymethyl-piperadine-N-2-ethane-sulfonate (HEPES, product of Nakarai Kagaku Co.). Culturing was carried out at 37° C. under aeration with 10% $CO_2$ and 90% air for 4 days. The human fetal fibroblasts attained a saturated cell concentration, so-called confluent condition, by the culturing.

$5 \times 10^8$ cells in the confluent condition were inoculated into MEM medium containing 10% FCS and culturing was carried out at 37° C. under aeration with 10% $CO_2$ and 90% air for 10 hours. The same culturing was carried out using the medium containing 100 ng/ml TPA.

Figure 9:
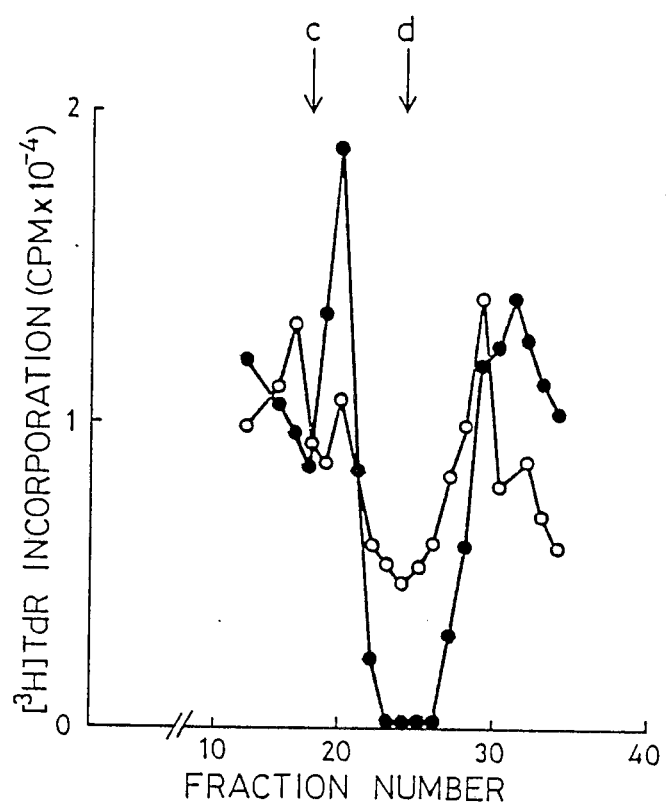
FIG. 9 shows Sephadex G 100 column chromatogram proving the increase of production of the present substance by TPA in Example 3.

Supernatant fluid was subjected to Sephadex G 100 column chromatography and elution in the same manner as in Example 1 to obtain the result illustrated in FIG. 9. As can be seen from the result, the production of the present substance is elevated by the addition of TPA.

The active fraction from the medium containing TPA was treated in the same manner as in Example 1 to obtain about 20 μg of the present substance.

EXAMPLE 4

Figure 10:
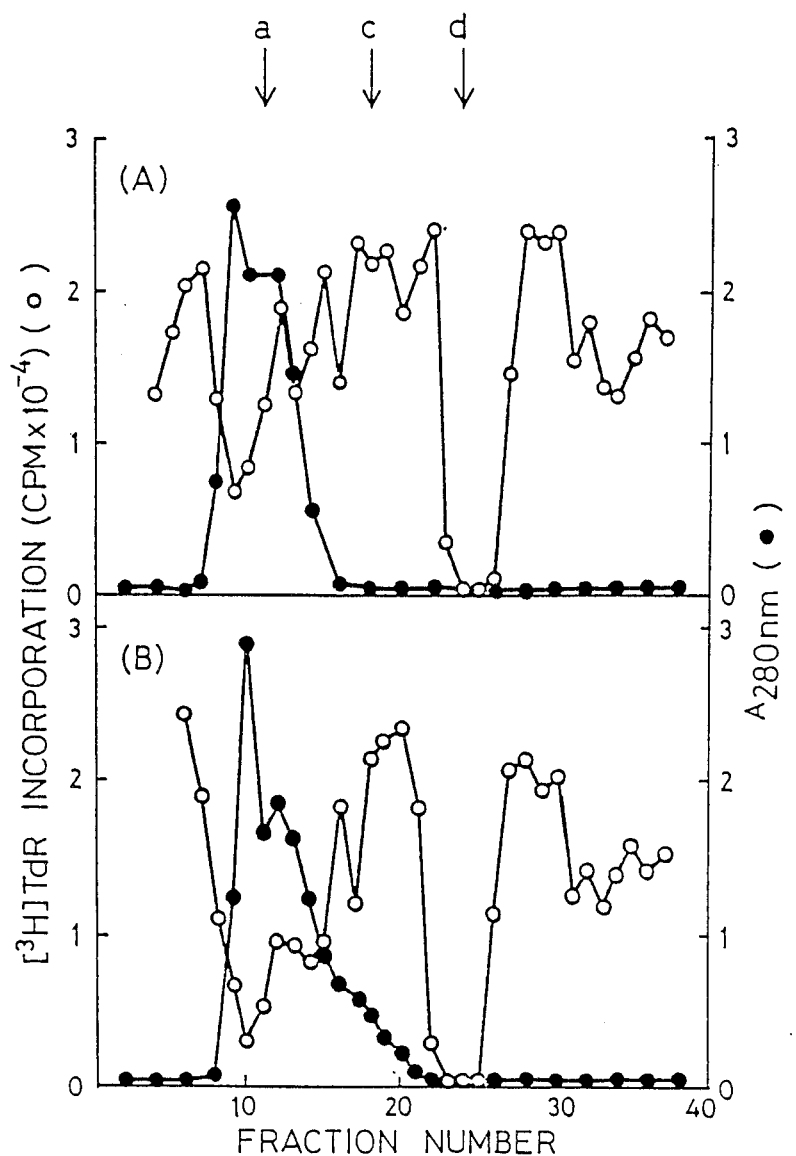
FIG. 10 shows the elution pattern on Sephadex G 100 chromatography of (A) fetal calf serum and (B) body fluid of *Bombyx mori* in Example 4.

Production of the present substances from fetal calf serum and body fluid of *Bombyx mori*:

25 ml each of fetal calf serum (product of GIBCO) and body fluid of *Bombyx mori* were mixed with 50 ml of cooled saturated ammonium sulfate (pH 7.5), respectively. The mixtures were allowed to stand at 4° C. for 1 hour. After centrifugation at 16,000 rpm for 15 minutes, the precipitates were dissolved in 5 ml of 10 mM phosphate buffer (pH 7.2) and put on Sephadex G 100 column (1.8×43 cm). Elution was carried out with the same phosphate buffer and the eluate was recovered in 5 ml fractions. Elution pattern is illustrated in FIG. 10.

Figure 11:
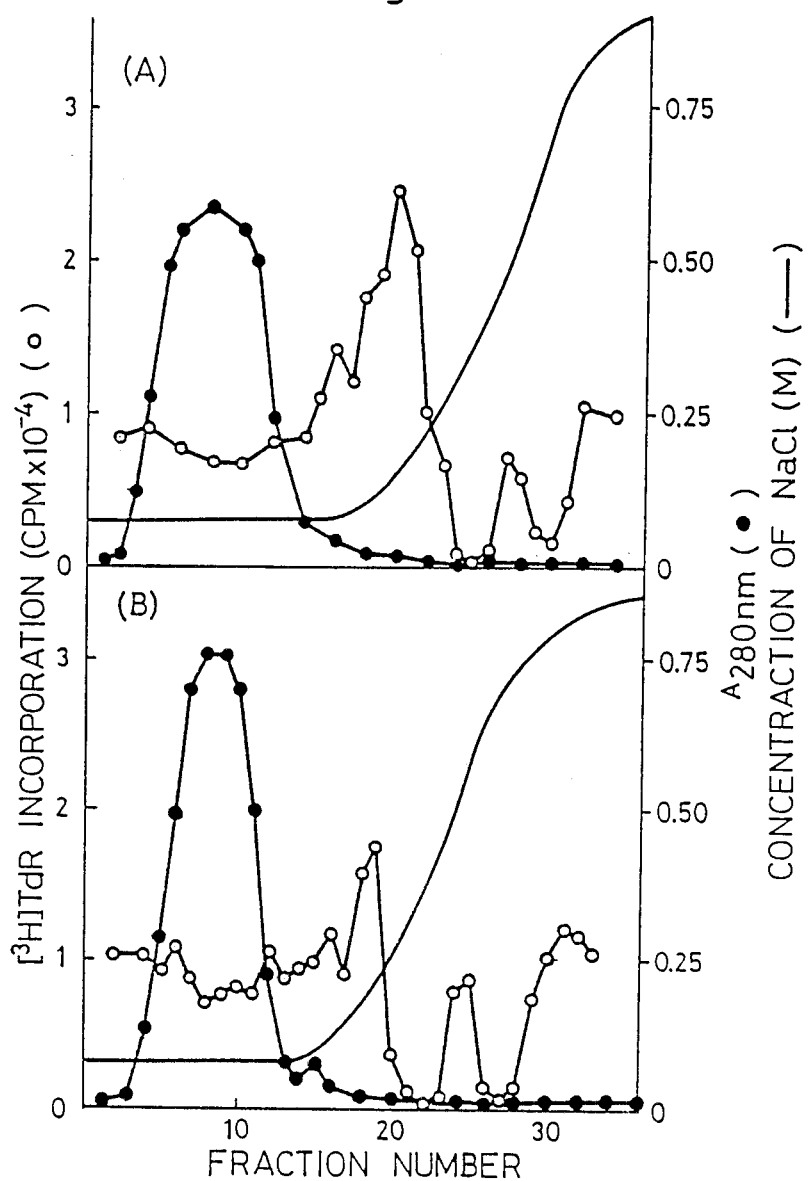
FIG. 11 shows the elution pattern on CM Sephadex (C5) chromatography of (A) fetal calf serum and (B) body fluid of *Bombyx mori* in Example 4.
Figure 12:
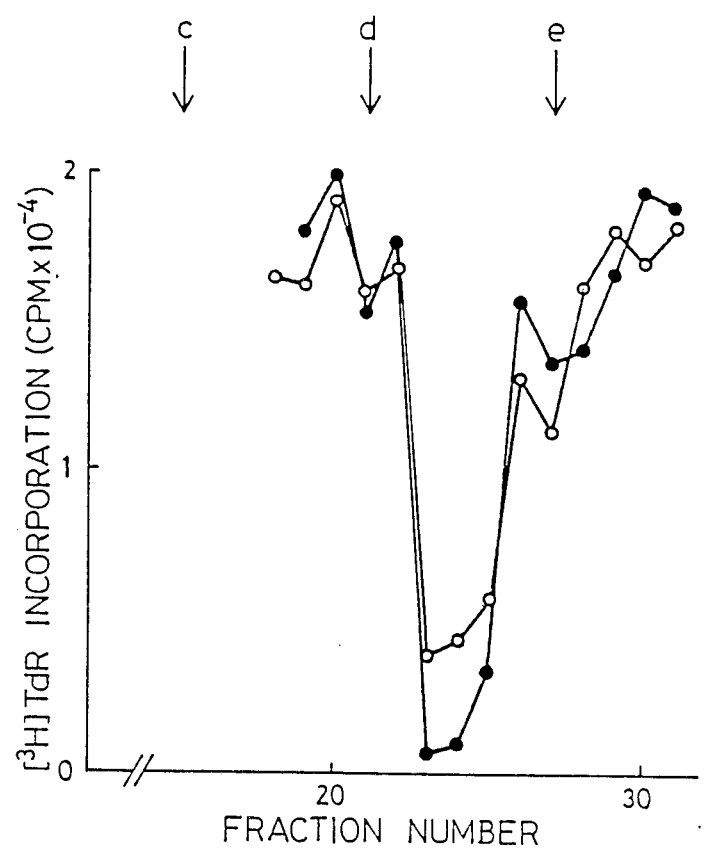
FIG. 12 shows the elution pattern on Sephadex G 50 chromatography of FCS I and Bm I in Example 4. Open and closed circles refer to the activity of DNA synthesis in lymphocytes by FCS I and Bm I, respectively.

The active fraction on Sephadex G 100 chromatography was diluted with twice as much distilled water as the fraction and subjected to CM Sephadex (C-25) column (1.8×10 cm) chromatography. The column was washed with about 30 ml of water containing 75 mM NaCl and elution was carried out under gradient of the concentration of saline solution (75 mM–1 M). The eluate was recovered in 2.5 ml fractions and the NaCl concentration of each fraction was measured with a conductivity meter. Elution pattern is illustrated in FIG. 11. The active fraction was concentrated with a rotary evaporator and subjected to Sephadex G 50 column (1.2×56 cm) chromatography. Elution was carried out with 0.1 M ammonium carbonate and the eluate was recovered in 1.25 ml fractions. The active fraction was lyophilized. Elution pattern of the fractions eluted with 0.3–0.4 M NaCl is illustrated in FIG. 12.

Figure 13:
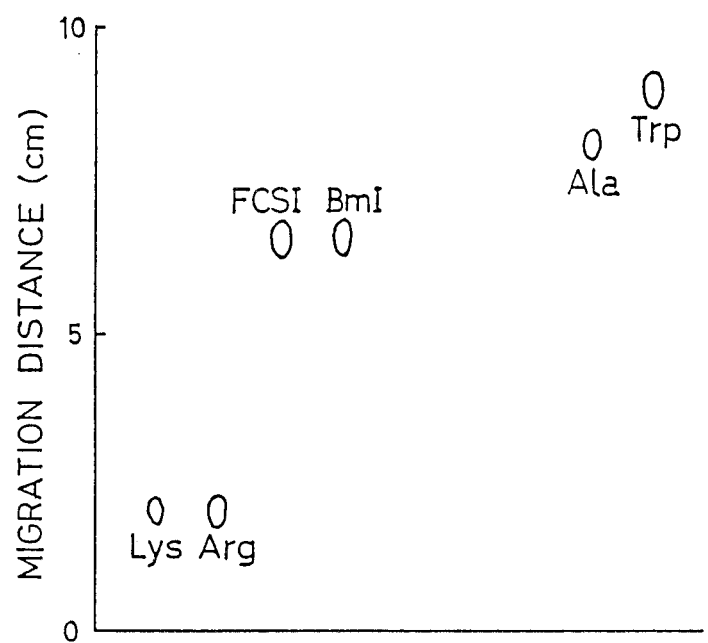
FIG. 13 shows the pattern of silica gel thin layer chromatography of FCS I and Bm I in Example 4.

For further purification, the active fraction dissolved in water was spotted on a silica gel thin layer plate (product of Merck & Co., Silica gel 60, 20×20 cm) and developed with a mixture of methanol and water (3:1) for about 2 hours. After development ninhydrin solution was spread on the thin layer plate followed by heating with a burner for 2-3 minutes to recognize the position of the peptide. The result is illustrated in FIG. 13. In the drawing, Lys, Arg, Ala and Trp refer to the amino acid markers, respectively, and FCS I and Bm I correspond to the present substances.

Figure 14:
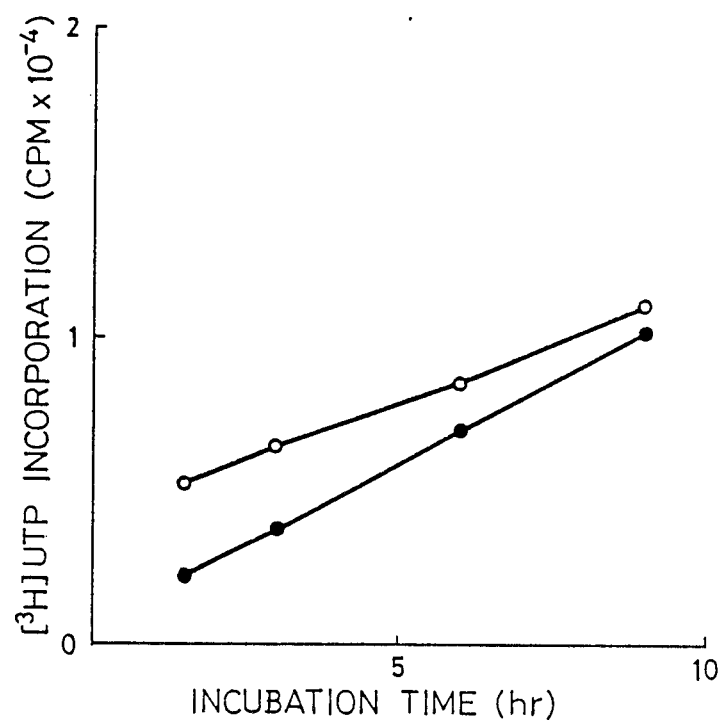
FIG. 14 shows the effect of FCS I on the UTP uptake by lymphocytes at early stage after lectin stimulation in Example 4.

Spleen cells were stimulated with lectin (concanavalin A:5 μg/ml and simultaneously 1 μCi of UTP was added to the cells. Culturing was carried out at 37° C. At the start of the culturing, 0.1 ml of the solution of combined FCS I active fractions No. 23–27 illustrated in FIG. 10 was added to examine the effect of FCS I on initial UTP uptake activity. The result is illustrated in FIG. 14. In the drawing, open and closed circles refer to the activities in the absence and presence of FCS I respectively.

EXAMPLE 5

Figure 15:
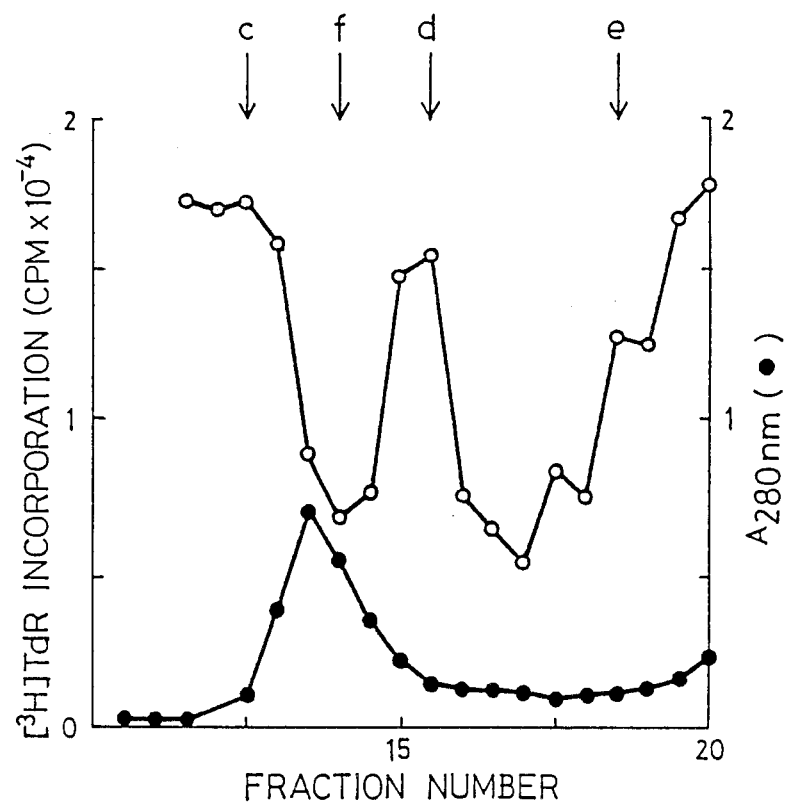
FIG. 15 shows Sephadex G 50 chromatography of culture supernatant of the fibroblast of *Bombyx mori* in Example 5. In the drawing, f refers to the molecular weight marker of insulin (5.7 Kd).

$2.5 \times 10^4$/ml fibroblast cells derived from *Antheraea eukarypti* established by Grace [Nature, 195, 788 (1962)] were cultured in 10 ml of Grace medium (product of GIBCO) containing 10% fetal calf serum at 37° C. under 5% $CO_2$ for 3 days. The medium was replaced with the fresh medium and culturing was continued for 3 days. Cells reached so-called confluent condition and were washed with 10 ml of Grace medium three times and cultured in Grace medium free of serum at 37° C. under 5% $CO_2$ for 3 days. The culture medium was recovered and put through Amicon Dia Flow Membrane (YM10, cut size:10,000 daltons). The filtrate was concentrated with a rotary evaporator and subjected to Sephadex G 50 column (1.8×48 cm) chromatography. Elution was carried out with 0.1 mM phosphate buffer (pH 7.2) and the eluate was recovered in 2.5 ml fractions. As illustrated in FIG. 15, a significantly high regulation activity against the DNA synthesis in lymphocytes was recognized at the position of a molecular weight of about 5,000 daltons (fraction Nos. 12–14), mainly at about 1,000 daltons (fraction Nos. 17–19). In FIG. 15, the open circles refer to the thymidine uptake into lymphocytes and the closed circles refer to the absorption at 280 nm of each fraction.

Figure 16:
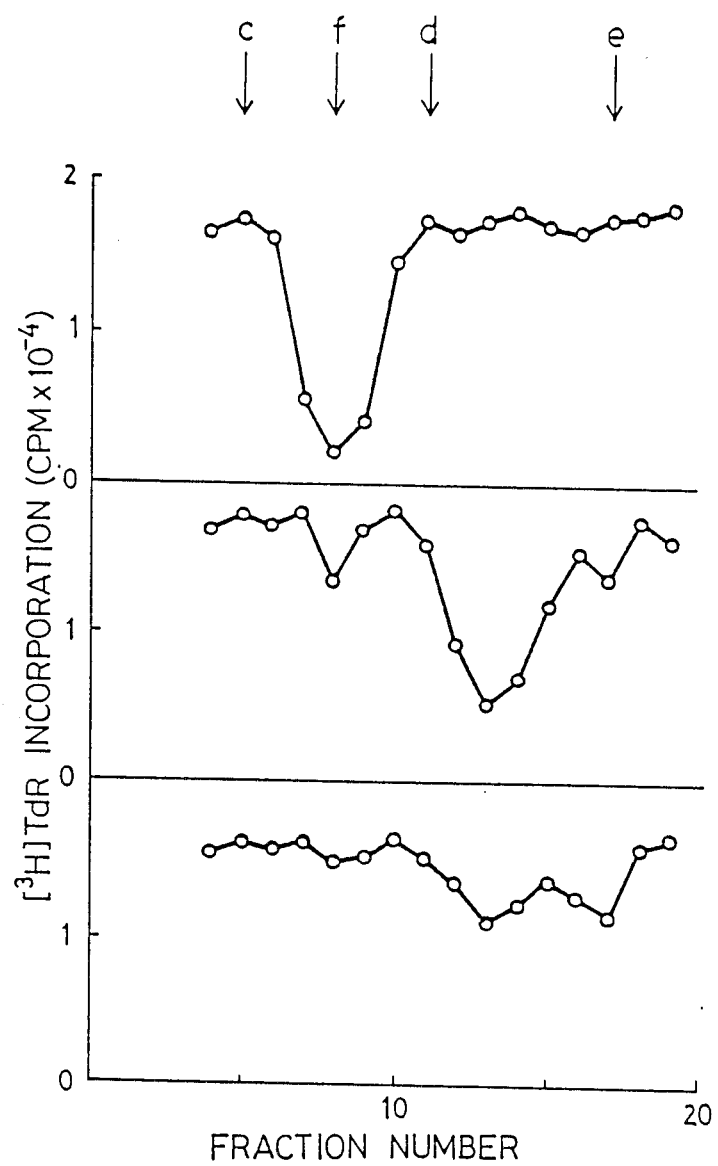
FIG. 16 shows the effect of trypsin treatment on the active factor in Example 5.

The activity at 5,000 daltons disappeared by incubation with 25 μg/ml trypsin at 30° C. and the activity was moved to the position of 1,000 daltons. By successive trypsin digestion, most of the activity disappeared (FIG. 16). In FIG. 16, the upper graph refers to the treatment free of trypsin, the middle graph incubation with trypsin for 30 minutes and the bottom graph incubation with trypsin for 1 hour.

Figure 17:
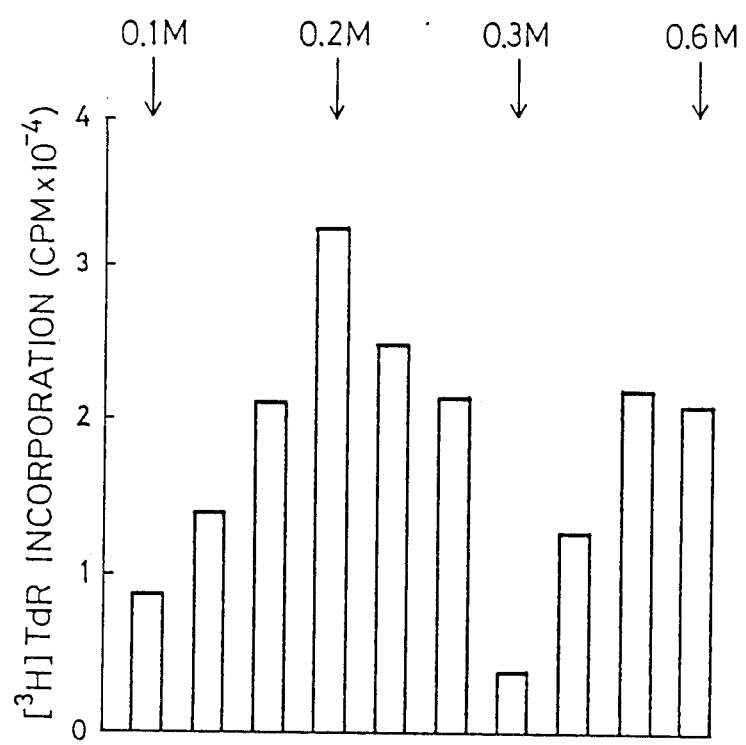
FIG. 17 shows CM Sephadex chromatography in Example 5.
Figure 18:
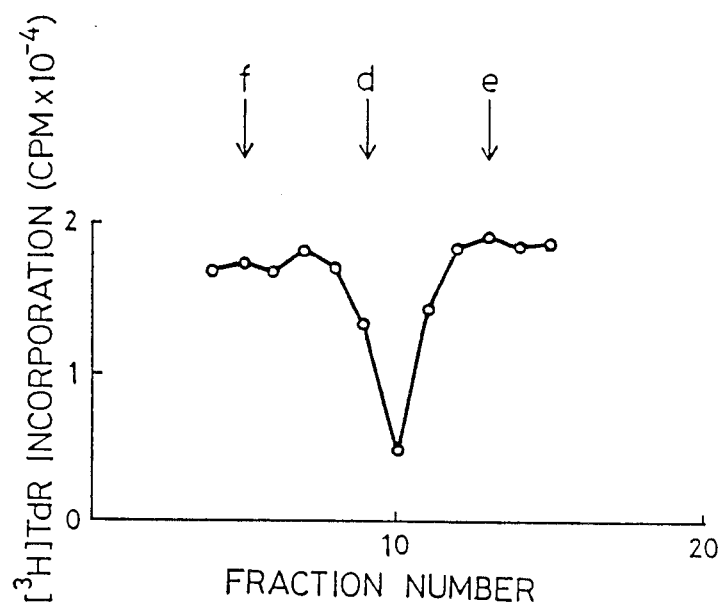
FIG. 18 shows Sephadex G 25 chromatography of Ae I in Example 5.
Figure 19:
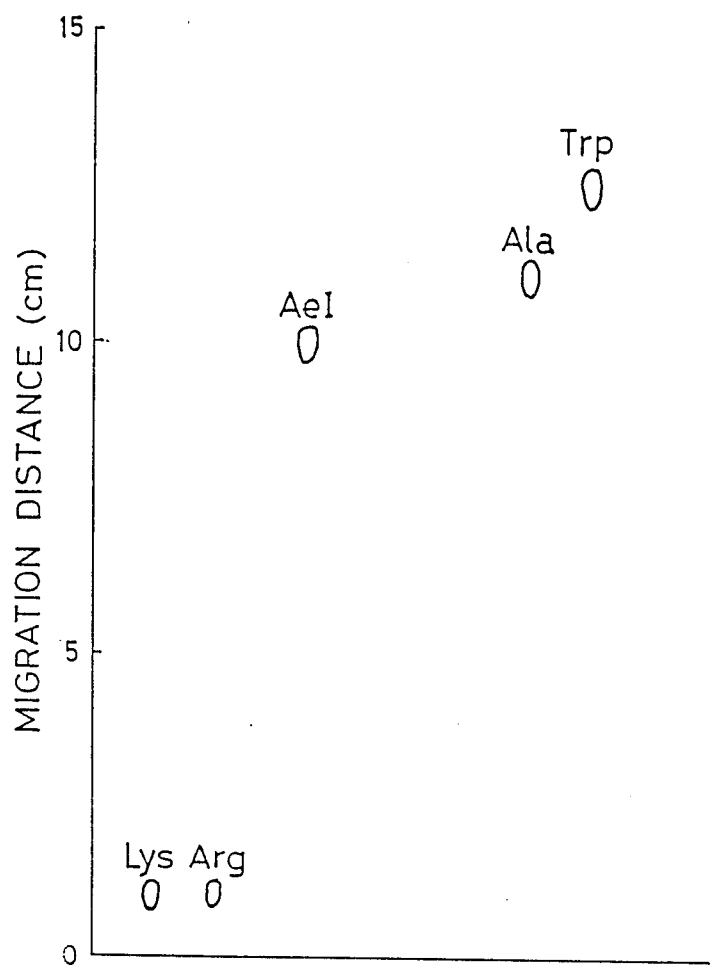
FIG. 19 shows silica gel thin layer chromatography of Ae I in Example 5.

The results mentioned above show that these factors are peptide-like substances. Further, the active fraction at a molecular weight of 1,000 daltons was subjected to CM Sephadex chromatography (10 ml). That is, CM Sephadex (gel bed:10 ml) in a centrifugation tube was equilibrated with 100 mM NaCl and fraction Nos. 17-19 in FIG. 15 were added to make a suspension. The suspension was allowed to stand at 4° C. for 15 minutes and after decantation of the supernatant fluid, the gel was washed with 10 ml of 0.1 M NaCl three times. The same procedure was repeated with 10 ml of water containing various concentrations (0.2–0.6 M) of NaCl. Each fraction diluted 4-fold with water was used to examine the DNA synthesis in lymphocytes. The result of CM Sephadex is illustrated in FIG. 17. In the drawing, the arrows refer to the concentration of NaCl. As is shown in FIG. 17, an active substance was eluted with about 0.4 M NaCl and the substance was named Ae I. The active substance was further purified by Sephadex G 25 chromatography to show that it has a molecular weight of about 1,000 daltons as illustrated in FIG. 18. The purity of the factor was examined by silica gel thin layer chromatography. That is, the active fraction containing Ae I in FIG. 18 was lyophilized and dissolved in water. The solution was spotted on silica gel thin layer chromatography. The plate was developed with a solution of methanol-water (3:1) and a ninhydrin solution was spread on the plate followed by heating with a burner for 3 minutes for color formation. Lys, Arg, Ala and Trp show the positions of the amino acid markers, respectively. Ae I exhibited a slightly delayed migration (FIG. 19) compared with alanine. Ae I in FIG. 19 corresponds to the present substance.

I claim:

1. A regulatory substance of T cell synthesis which inhibits DNA synthesis of T cells, said substance being a protein which has the following physicochemical properties:

Elementary analysis:Having the elements C, H, O, N and S

Molecular weight:About 1,000 daltons

Thermostability:Stable the several months at −20° C., for 30 minutes to 1 hour at 56° C., and for 30 minutes at 100° C.

Distinction on acidic, basic or neutral properties:- Weakly basic pH stability:Stable at pH 3.5–10.0

Ultraviolet spectrum:Maximum absorption at 210–220 nm

Color reaction:Ninhydrin positive

Solubility in solvents:Readily soluble in water, ethanol and methanol

Color of substance:Colorless in water, ethanol and methanol.

2. The regulatory substance of T cell DNA synthesis according to claim 1, which is obtained by culturing fibroblasts or lymphocytes of animals or insects in a medium, forming and accumulating a regulatory substance of T cell DNA synthesis in the culture broth and recovering the regulatory substance of T cell DNA synthesis therefrom.

3. The regulatory substance of T cell DNA synthesis according to claim 2, wherein the animal belongs to mammals.

4. The regulatory substance of T cell DNA synthesis according to claim 3, wherein the animal is a mouse, a rat or a human.

5. The regulatory substance of T cell DNA synthesis according to claim 2, wherein the medium is selected from RPMI 1640 medium and MEM medium which are free of serum or contains fetal calf serum.

6. The regulatory substance of T cell DNA synthesis according to claim 2, wherein the medium contans at least one of the phorbol esters selected from phorbol myristate, phorbol-13-acetate and 12-O-tetradecanoyl-phorbol-13-acetate.

7. The regulatory substance of T cell DNA synthesis according to claim 1, which is obtained by recovering from the serum of mammals or body fluids of insects.

8. The regulatory substance of T cell DNA synthesis according to claim 7, the serum of mammals is selected from the serums of humans, bovines, rats and mice.

9. The regulatory substance of T cell DNA synthesis according to claim 7, the body fluid of insects is selected from the body fluids of Bombyx, Antheraea, Sarcophaga and Apis.

* * * * *

UNITED STATES PATENT AND TRADEMARK OFFICE
CERTIFICATE OF CORRECTION

PATENT NO. : 4,613,458
DATED : September 23, 1986
INVENTOR(S) : YASUJI OKAI

It is certified that error appears in the above-identified patent and that said Letters Patent is hereby corrected as shown below:

Column 5, line 22, change "stoped" to --stopped--

Column 5, line 47, change "[$^3$]" to --[$^3$H]--

Column 5, line 49, change "[$^3$]" to --[$^3$H]--

Column 7, line 34, change "(C5)" to --(C25)--

Column 7, line 63, change "$10^8$" to --10 ml--

Column 10, line 15, change "µg/ml" to --µg/ml)--

Column 11, line 31, change "Stable the" to --Stable for--

Column 12, line 24, change "contans" to --contains--

Signed and Sealed this

Sixteenth Day of December, 1986

Attest:

DONALD J. QUIGG

Attesting Officer

Commissioner of Patents and Trademarks